(12) United States Patent
Brulez et al.

(10) Patent No.: US 7,700,147 B2
(45) Date of Patent: Apr. 20, 2010

(54) BIOMIMETIC PROSTHETIC LIGAMENT AND PRODUCTION METHOD THEREOF

(75) Inventors: Bernard Brulez, Bourbonne les Baines (FR); Jacques-Philippe Laboureau, Le Tignet (FR); Veronique Migonney, Eaubonne (FR); Mihaela Ciobanu, Iasi (RO); Graciela Pavon-Djavid, Puteaux (FR); Alain Siove, Sousy Sous Montmorency (FR)

(73) Assignee: LARS- Laboratoire d'Application et de Recherche Scientifique, Arc-sur-Tille (FR)

( * ) Notice: Subject to any disclaimer, the term of this patent is extended or adjusted under 35 U.S.C. 154(b) by 1218 days.

(21) Appl. No.: 10/542,620

(22) PCT Filed: Jan. 19, 2004

(86) PCT No.: PCT/FR2004/000103

§ 371 (c)(1),
(2), (4) Date: Jul. 18, 2005

(87) PCT Pub. No.: WO2004/067051

PCT Pub. Date: Aug. 12, 2004

(65) Prior Publication Data

US 2006/0136057 A1    Jun. 22, 2006

(30) Foreign Application Priority Data

Jan. 17, 2003   (FR) .................... 03 00495

(51) Int. Cl.
*A61F 2/02* (2006.01)
*A61F 2/08* (2006.01)
*B05D 3/10* (2006.01)

(52) U.S. Cl. .............. 427/2.1; 427/2.24; 427/2.25; 427/2.26; 427/2.27; 427/299; 427/307; 427/322; 623/11.11; 623/13.11

(58) Field of Classification Search ............. 427/2.1, 427/2.24, 299, 307, 2.26, 2.27, 322; 623/11.11, 623/13.11

See application file for complete search history.

(56) References Cited

U.S. PATENT DOCUMENTS

| 4,743,258 | A | | 5/1988 | Ikada et al. | |
|---|---|---|---|---|---|
| 5,290,548 | A | * | 3/1994 | Goldberg et al. | 424/78.18 |
| 6,143,354 | A | * | 11/2000 | Koulik et al. | 427/2.24 |
| 6,200,626 | B1 | | 3/2001 | Ammon et al. | |
| 6,306,419 | B1 | * | 10/2001 | Vachon et al. | 424/422 |
| 6,361,819 | B1 | * | 3/2002 | Tedeschi et al. | 427/2.24 |
| 2002/0169493 | A1 | * | 11/2002 | Widenhouse et al. | 623/1.1 |
| 2003/0023318 | A1 | * | 1/2003 | Simmoteit et al. | 623/23.76 |

FOREIGN PATENT DOCUMENTS

| EP | 454599 A | * | 10/1991 |
|---|---|---|---|
| EP | 0 727 233 | | 8/1996 |
| EP | 0 891 998 | | 1/1999 |

* cited by examiner

*Primary Examiner*—Timothy H Meeks
*Assistant Examiner*—Cachet I Sellman
(74) *Attorney, Agent, or Firm*—Young & Thompson

(57) ABSTRACT

Biomimetic artificial prostheses which are made from polyester, such as polyethylene terephthalate, and a method for the biomimetic functionalization of such prostheses. The method includes a step involving the grafting of biologically-active polymers or copolymers to the polyester surface of the prostheses, the grafting step consisting of the peroxidation of the surface by ozonation followed by a step including the radical polymerization of a solution of at least one monomer. The method also includes an optional step consisting in impregnating the prostheses with type I and/or II collagen and/or fibronectins. The prostheses thus obtained enable a normal and uniform regrowth of the fibroblasts, thereby significantly improving the biological integration of such polyester prostheses.

25 Claims, No Drawings

BIOMIMETIC PROSTHETIC LIGAMENT AND PRODUCTION METHOD THEREOF

This is a 371 National Stage application of International application no. PCT/FR2004/000103, filed Jan. 19, 2004, which claims priority to French application no. 03/00495, filed Jan. 17, 2003. The entire contents of the Above-referenced applications are hereby incorporated by reference in their entirety.

The present invention relates to a biomimetic prosthetic ligament as well as to the method for obtaining it.

BACKGROUND OF THE INVENTION

Artificial ligaments for replacing biological articular ligaments, and notably those of the knee, are in certain specific cases preferred to direct suture for reconstruction by autogenously grafting. Indeed, the quality of these ligaments both on the mechanical level and on that of biocompatibility has considerably improved over the last twenty years.

Thus, for example, a prosthetic ligament in polyethylene terephtalate (PET) said to be with <<orientated fibres>> is known from French Patent FR-96 14263. This ligament consists of a cloth rolled or folded over itself, which cloth includes two extreme intra-bone portions and an intermediate intra-joint portion formed by a hank of longitudinal adjacent active weft yarns not bound to each other transversally. Upon mounting the ligament, a longitudinal twist is given to each active yarn, resulting in a dextrogyral or levogyral ligament reproducing the natural kinking of the ligaments in flexion. This type of ligament in PET, a material whose biocompatibility is well known, has an extremely high resistance to tensile, flexural and torsional stresses, leaving the presumption of a larger life expectancy than that of the known ligaments.

However, in spite of these considerable advances on the biomechanical level, failures of these artificial ligaments are still reported in patients. Investigations carried out on the causes of these failures, have demonstrated poor regrowth of fibroblasts after implantation. Indeed, the distribution of these cells is inhomogeneous at the surface of the ligament, fibroblasts not growing in the intra-bone prosthetic areas and clustering on the fibres of the intra-joint area. Further, these fibroblasts have an abnormal rounded morphology, with very little anchoring points at the surface of the ligament. Secretion of collagen by these cells is in fact erratic and causes individualization of the fibres of the intra-joint area with accumulation of fibrous tissues between the envelope and the central portion of the prostheses, thereby contributing to their failure.

Confronted with this problem of providing good fibroblastic rehabilitation of prostheses, French Patent FR 2 651 994 proposes impregnation of the prosthetic ligament with collagen, collagen fibres being orientated along the longitudinal axis of the ligament in order to obtain a proper direction for its rehabitation by a living conjunctive tissue. In addition to limited and not very satisfactory efficiency, this solution has the major drawback of depending on the quality of the collagen used which is difficult to reproduce.

SUMMARY OF THE INVENTION

The present invention is therefore directed to finding a remedy to these problems by proposing a method for biomimetic functionalization of ligaments, notably, a method notably providing them with the capacity of mimicking living materials in order to improve their biological integration.

In this respect and according to the invention, a method for biomimetic functionalization of polyester, notably polyethylene terephtalate (PET), prostheses is proposed and is remarkable in that it includes at least one step for grafting biologically active polymers or copolymers at the polyester surface of said prostheses, which grafting step consists of performing peroxidation of the surface by ozonation followed by a radical polymerization step of a solution of at least one monomer. It will be noted that by polyester prosthesis, is meant any prosthesis formed of PET or polyester derivative fibres giving adequate performances for its use in ligaments as well as any prosthesis having at its surface or at that of its fibres, a polyester and notably PET layer.

DETAILED DESCRIPTION OF THE INVENTION

It well understood that by creating at the surface of a ligament made according to the aforementioned French Patent FR-96 14263, a <<carpet>> of active biological polymers, its cellular adherence and proliferation properties are thereby modified, making them favourable for a normal and homogenous fibroblastic rehabitation, as shown by the obtained cell culture results.

Moreover, these properties may be improved by proceeding according to another feature of the invention, with an additional step for preparing the polyester surface in a solvent medium alone or in a solvent medium followed by an aqueous medium, which precedes the grafting step.

These two alternatives of this preparation step considerably contribute to improving the efficiency of the grafting step, by enhancing the quality of the grafted surface as well as the amount of grafted (co)polymers. They also play a not insignificant role in the biocompatible character of the thereby treated ligament.

Other advantages and features will become better apparent from the description which follows of a complete alternative embodiment, given as a non-limiting example, of the functionalization method according to the invention.

The method according to the invention is applied here to already formed ligamentous prostheses or even to polyester tissue wefts involved in the manufacturing of said prostheses; this method is split up according to the following steps:

Step 1: Preparation of the Polyester Surface

1A) In a Solvent Medium:

This so-called degreasing step is required for removing greases and impurities, incorporated during the manufacturing of the polyester weft used as a structure for the ligament. It thereby allows pathological reactions of the acute synovitis type to be avoided during implantation in the patient. Further, with this step, growth of the fibroblasts may be provided on a thereby cleaned polyester surface, a growth which is not observed on uncleaned surfaces.

Two alternatives of this preparation in a solvent medium are distinguished according to the nature of the selected solvent.

Alternative 1: Degreasing Without any Swelling of the Surface:

A minimum of 12 extraction cycles is applied in a SOHXLET apparatus and a check for fat residues is performed after the $12^{th}$ cleaning cycle with hexane. These cleaning cycles with hexane are followed by washing cycles with ethyl ether (RPE), a minimum of three washings with checking for residues after the third washing.

Alternative 2: Degreasing with a Solvent Capable of Causing the Polyester Surface to Swell:

The use of a solvent capable of causing the polyester surface to swell provides the advantage of improving grafting by increasing the number of peroxides on the treated surface during the ozonation step.

Such a solvent has the characteristic of having a dielectric constant larger than 30. Preferably, this solvent is of the cyclic or aliphatic ether type. Further, it will be selected from the following solvent group: tetrahydrofurane (THF), dimethylsulfoxide (DMSO), N,N-dimethylformamide (DMF), N,N-dimethylacetamide (DMA), N-methylpyrrolidone (NMP). These solvents have the advantage of having low or zero toxicity and so that they may easily be used in an industrial environment.

The treatment is performed by immersing polyester parts into the solvent for a time of the order of 5 minutes to about 1 hour, preferably within 10-25 minutes. Thus, as an example, a time of 15 minutes at room temperature will be selected for immersion in tetrahydrofurane (THF).

1B) In an Aqueous Medium:

The goal of this optional step for preparing the surface in an aqueous medium is to remove the residues from the manufacturing of the polyester, present at its surface, such as low molecular weight organic acids such as for example terephtalic acid for PET. A perfectly finished surface is thereby obtained before ozonation.

The treatment consists of washing the polyester parts in a 5% by weight solution of sodium carbonate ($Na_2CO_3$) in distilled water. This washing is carried out under hot conditions, i.e., at a temperature higher than 60° C. and less than 120° C. and preferably with slight boiling, i.e., 100° C.±5° C., for tens of minutes. Of course, any other alkaline or alkaline-earth carbonate such as $K_2CO_3$ or $CaCO_3$ may be used. The washing is followed by successive rinsings with distilled water until the pH of the rinsed water has returned to 7.

1C) Cleaning:

Regardless of the steps carried out earlier (alternative 1 or alternative 2 of step 1A, then step 1B, or only step 1A), the polyester product is then cleaned, for example by rinsing it with absolute ethanol or tetrahydrofurane (THF) followed by oven-drying for a period of 30 minutes, for example.

Step 2: Grafting Biologically Active Polymers or Copolymers on the Polyester Surface:

1A) Selection and Preparation of the Monomers:

The monomers used according to the invention are monomers capable of radical polymerization and copolymerization giving rise to biocompatible polymers stimulating cellular proliferation and differentiation and more particularly that of the fibroblasts. Such monomers containing carboxylate, phosphate, sulfonate and sulfate groups are, for example, described in U.S. Pat. No. 6,365,692 and may be used according to the invention, alone or as a mixture. Methacrylic acid and styrene sulfonate will be used preferably, as well as their mixtures. Before using them for the polymerization, these monomers will first be purified. Thus, for example, for sodium styrene sulfonate, it is purified by recrystallization from a mixture of bidistilled water/alcohol (10:90, v:v), and then it is dissolved at 70° C. in this solution. It is then filtered in vacuo with a sintered glass disk having a porosity index of 3 and it is kept at 4° C. The formed sodium sulfonate crystals are collected by filtration and the obtained solid is dried in vacuo at 50° C. until a constant weight is obtained.

2B) Ozonation:

The prostheses or the constitutive polyester wefts of these pre-treated prostheses according to the step 1 are introduced in an ozonation device as used conventionally.

For example, a tubular reactor of 500 cm³ containing 100 cm³ of bidistilled water may be used, which reactor is provided with an ozone feeder plunger tube. For example, an ozone gas flux equivalent to 50 g/m³ of oxygen may be used. For such an amount of ozone, the optimum time for ozonation of PET is from 20 to 90 minutes. Measurements of the peroxide rates show that the optimum rate is obtained between 30 and 60 minutes of ozonation, always for this same ozone flux. It will also be noted that an ozonation time of more than 90 minutes strongly deteriorates the PET surface.

Moreover, the contribution of alternative 2 of step 1A will be reported. Indeed, the use of a solvent capable of causing the surface to swell increases the peroxide rate by a factor 5, relatively to the use of a solvent without any swelling. Once ozonation is completed, the prostheses or the polyester weft introduced into the ozonation device are rinsed and cleaned, for example according to the following protocol: rinse three times with bidistilled water, then three times with absolute alcohol, and then three times with tetrahydrofurane (THF). Next, dry in a vacuum oven for 30 minutes at 25° C.

2C) Polymerization:

The selected monomer(s), prepared according to step 2A are put into solution in water, preferably bidistilled water. Any concentration compatible with the application of the radical polymerization reaction may be selected with a minimum of 5% by weight. Advantageously, concentrations close to the solubility limit of the monomer(s) in the solution will be selected, with a viscous medium thereby promoting radical polymer propagation reactions relatively to termination reactions: grafted polymer chains with a larger size are thereby obtained. This amounts to selecting a weight concentration $k=s-\in$, where s is the solubility limit and $\in$ is 1-7% by weight. Thus, for example, in the case of polystyrene sulfonate, the solubility limit of which is 20% by weight, a concentration of 15% will be selected.

The duration of the polymerization step depends on the nature of the monomer. It is estimated as being the time required for gelling of the medium at the reaction temperature. Thus, for example, it will be recalled that for polystyrene sulfonate at 70° C., polymerization will last 1 hour and at 65° C. it will last 1 hour 30 minutes.

The polymerization reaction is conducted in a sealed chamber and cleared of any oxygen, for example, by argon bubbling. The solution of monomers or comonomers which are intended to react and the prostheses or pre-ozonated polyester tissue strips are introduced into this chamber. The sealed container is heated in a water bath at the determined temperature and for the determined time as discussed earlier.

At the end of the reaction, the polyester components which have been grafted are extracted from the reactor. These grafted materials may then be washed in order to notably remove residues of monomer(s) which have not reacted. For example, the functionalized surface may be washed several times with an adequate solvent of the monomer(s), for example by distilled water, and optionally the washing may be completed with any adequate solvent, absolute ethanol for example, in order to remove possible traces of non-grafted polymers.

Step 3: Impregnation with Biochemical Agents:

This step is optional. It aims at reinforcing the biological integration capacity of the ligament to which biomimetic polymers have been grafted previously, as discussed in steps 1 and 2. Thus, impregnation of the prosthesis by one or more biochemical agents aims at enhancing its cellular adherence and proliferation properties. These biochemical agents promoting colonization by fibroblasts are a protein of the family of fibronectins and/or collagen of type I and/or III. A mixture of the previous proteins, i.e., a mixture of fibronectins and collagen of type I and/or III will be used advantageously: a synergetic effect is observed on the adherence of the fibroblasts. Impregnation of the prosthesis by these agents may for example be carried out by soaking it in a bath containing collagen.

It is self-evident that this impregnation step does not inevitably follow the grafting step and that it may be inserted and interposed between other steps for preparing the ligament according to its manufacturing stage. In addition, this impregnation step will advantageously be followed by a step for sterilizing the ligament.

In order to measure the efficiency of the method which has just been described, comparative tests were conducted on portions of tissues made with knitted PET fibres, the polyester being semi-crystalline with a crystallinity rate of 40%±5% and a melting temperature close to 260° C.±5° C. These fibre tissues are constitutive of artificial ligaments as manufactured and marketed by the applicant. Non-grafted control PET fibres and two types of PET fibres grafted with sodium polystyrene sulfonate and also grafted with an equiponderant mixture of methacrylic acid (AM) and sodium styrene sulfonate (SSNa) were thereby prepared. The different conditions of preparation will be found in Table 1.

TABLE 1

Preparation of the samples

| | Preparation of the surface | Ozonation | Grafting |
|---|---|---|---|
| Non-grafted PET fibre | Hexane and ethyl ether; 5% $Na_2CO_3$ | — | — |
| Grafted PET fibres (1) | THF: 15 min; $Na_2CO_3$: 5% | 60 min at 50 g $O_3/m^3O_2$ | 15% by weight SSNa solution; 1 h 30 min at 65° C. |
| Grafted PET fibres (2) | THF: 15 min; $Na_2CO_3$: 5% | 60 min at 50 g $O_3/m^3O_2$ | 15% SSNa and 15% AM (by weight) solution; 1 h 30 min at 65° C. |

Next, different tests for biological evaluation and notably for fibroblast cultures, and for the adherence of fibroblasts on these different surfaces were performed and the obtained results appear in the Table hereafter:

TABLE 2

Biological evaluation

| Parameters | Non-grafted PET | Grafted PET (1) and (2) |
|---|---|---|
| Number of confluent cells (culture in 24-well-plates) | $1.10^5$ cells/well | $1.10^5$ cells/well |
| Development of fibroblasts | Inhomogeneous cluster distribution along the fibres | Homogeneous distribution over the whole surface of the tissue |
| Morphology | Rounded shape | Elongated and spread-out shape |
| Adherence force (relative unit) | 1 | 5-8 |
| Adsorption of collagen of type I (relative proportions in $ng/cm^2$) | 100 | 143 |

It is therefore observed that the grafting of biomimetic polymers and in particular of styrene sulfonate at the surface of polyester ligaments provides normal and homogeneous development of fibroblasts on this surface.

Additionally, it will be reported that the treated surface has a higher affinity towards proteins, with which better adsorption of collagen and other biochemical factors promoting colonization by fibroblasts may be obtained. It is therefore well understood that ligaments, the surface of which will have been treated according to steps 1 and 2 of the method, and which have then undergone step 3 for impregnation with such biochemical factors, will still see their capacities of causing the fibroblasts to adhere and to properly orientate their development, improve significantly.

Finally, it is self-evident that the biomimetic functionalization method according to the invention may be applied to any type of polyester prosthesis for which improvement of biological integration is desired and that the examples which have just been given are only particular illustrations and by no means limit the fields of application of the invention.

The invention claimed is:

1. A method for treating polyester artificial prostheses, said method comprising:
   (i) a first step of preparing a polyester surface of said prostheses in a solvent consisting of hexane that does not cause the polyester surface to swell, and
   (ii) grafting one or more biologically active polymers or copolymers to the polyester surface of said prostheses prepared in step (i), wherein said grafting step consists of achieving peroxidation of the polymer surface by ozonation followed by a radical polymerisation of a solution of at least one monomer, wherein,
   said method achieves biomimetic functionalization so that the prostheses is adapted to mimic living materials and facilitate anchoring and development of fibroblasts after implantation of said prostheses,
   said method optionally comprises one or more washings with ethyl ether after the step of preparing in the solvent in step (i), and
   said polyester artificial prostheses comprises a polyethylene terephtalate material.

2. The method according to claim 1, wherein the polyethylene terephtalate is semi-crystalline.

3. The method according to claim 1, wherein the ozonation time for an ozone content of the order of 50 $g/cm^3$ is between 20 and 90 min.

4. The method according to claim 1, wherein said at least one monomer is sodium styrene sulfonate.

5. The method according to claim 1, wherein the solution of at least one monomer has a concentration of monomer(s) between 5% and k%, where k is a concentration close to the solubility limit of the monomer(s) in the solution.

6. The method according to claim 1 wherein the preparation of the polyester surface in the solvent in step (i) is followed by an additional preparation step in an aqueous medium before proceeding with grafting.

7. The method according to claim 6, wherein the step for preparing the polyester surface in an aqueous medium consists of treating the polyester surface with an aqueous solution of alkaline or alkalineearth carbonate salts at a temperature of 60-120° C. in order to remove residues from the manufacturing of the polyester present at the surface of the polyester.

8. The method according to claim 1, further comprising an additional step for impregnating the prosthesis after the grafting step with one or more biochemical agents promoting colonization by fibroblasts.

9. The method according to claim 8, wherein the one or more biochemical agents is a protein of the family of fibronectins and/or collagen of type I and/or III.

10. The method according to claim 7, wherein said aqueous solution comprises $Na_2CO_3$ or $CaCO_3$.

11. The method of claim 7, wherein said washing with an aqueous solution of alkaline or alkaline-earth carbonate salts is performed at a temperature of 100° C. +/−5° C. for ten minutes.

12. The method according to claim 1, which further comprises, after step (i), cleaning the polyester surface by rinsing with absolute ethanol or tetrahydrofurane.

13. A biomimetic functionalization method for treating polyester artificial prostheses, said method comprising:
   (i) a first step of preparing a polyester surface of said prostheses in a solvent medium that causes the polyester surface to swell;
   (ii) preparing the polyester surface of said prostheses in an aqueous medium after the preparation of the polyester surface in the solvent medium in step (i); and
   (iii) grafting one or more biologically active polymers or copolymers to the polyester surface of said prostheses after step (ii), said grafting step consisting of achieving peroxidation of the polymer surface by ozonation followed by a radical polymerisation of a solution of at least one monomer, wherein,
   the preparation of the polyester surface in an aqueous medium in step (ii) consists of treating the polyester surface with an aqueous solution of alkaline or alkalineearth carbonate salts at a temperature of 60-120° C. in order to remove residues from the manufacturing of the polyester present at the surface of the polyester,
   said method achieves biomimetic functionalization so that the prostheses is adapted to mimic living materials and facilitate anchoring and development of fibroblasts after implantation of said prostheses, and
   said polyester artificial prostheses comprises a polyethylene terephtalate material.

14. The method according to claim 13, wherein the solvent medium able to modify the polyester surface by swelling is of the cyclic or aliphatic ether type with low or zero toxicity.

15. The method according to claim 13, wherein the solvent medium able to modify the surface by swelling has a dielectric constant larger than 30.

16. The method according to claim 13, wherein the solvent medium able to modify the surface by swelling is selected from the group consisting of: tetrahydrofurane (THF), dimethylsulfoxide (DMSO), N,N-dimethylformamide (DMF), N,N-dimethylacetamide (DMA), and N-methylpyrrolidone (NMP).

17. The method according to claim 13, wherein the polyethylene terephtalate is semi-crystalline.

18. The method according to claim 13, wherein the ozonation time for an ozone content of the order of 50 $g/cm^3$ is between 20 and 90 min.

19. The method according to claim 13, wherein said at least one monomer is sodium styrene sulfonate.

20. The method according to claim 13, wherein the solution of at least one monomer has a concentration of monomer(s) between 5% and k%, where k is a concentration close to the solubility limit of the monomer(s) in the solution.

21. The method according to claim 13, wherein said aqueous solution comprises $Na_2CO_3$ or $CaCO_3$.

22. The method of claim 13, wherein said washing with an aqueous solution of alkaline or alkalineearth carbonate salts is performed at a temperature of 100° C. +/−5° C. for ten minutes.

23. The method according to claim 13, further comprising an additional step for impregnating the prosthesis after the grafting step with one or more biochemical agents promoting colonization by fibroblasts.

24. The method according to claim 23, wherein the one or more biochemical agents is a protein of the family of fibronectins and/or collagen of type I and/or III.

25. The method according to claim 13, which further comprises, after step (i), cleaning the polyester surface by rinsing with absolute ethanol or tetrahydrofurane.

* * * * *